United States Patent [19] [11] 4,103,643
Staunton [45] Aug. 1, 1978

[54] AEROSOL-REDUCING SLIDE HOLDER SYSTEM
[75] Inventor: John J. J. Staunton, Oak Park, Ill.
[73] Assignee: The Perkin-Elmer Corporation, Norwalk, Conn.
[21] Appl. No.: 809,504
[22] Filed: Jun. 23, 1977

Related U.S. Application Data
[63] Continuation of Ser. No. 428,295, Dec. 26, 1973, abandoned, which is a continuation of Ser. No. 341,347, Mar. 15, 1973, abandoned.

[51] Int. Cl.² ............................................. B05C 11/08
[52] U.S. Cl. ........................................ 118/50; 118/52; 118/501; 269/21
[58] Field of Search .................................. 118/52–56, 118/50, 50.1, 320, 321, 326; 427/2, 238, 240, 241; 34/8, 58, 59; 269/21

[56] References Cited
U.S. PATENT DOCUMENTS

| 1,368,338 | 2/1921 | House, Jr. | 118/320 X |
| 1,811,395 | 6/1931 | Hoxie et al. | 118/52 X |
| 2,386,591 | 10/1945 | Campbell | 118/52 |
| 2,876,573 | 3/1959 | Schmidt | 34/58 |
| 3,280,792 | 10/1966 | Heyde | 118/52 |
| 3,389,682 | 6/1968 | Gardner | 269/21 X |
| 3,426,727 | 2/1969 | Balain et al. | 279/3 X |
| 3,538,883 | 11/1970 | Polin | 118/50 X |
| 3,577,267 | 5/1971 | Preston, Jr. et al. | 118/56 X |
| 3,705,048 | 12/1972 | Staunton | 118/52 X |
| 3,730,134 | 5/1973 | Kadi | 118/50 |

Primary Examiner—Morris Kaplan
Attorney, Agent, or Firm—Salvatore A. Giarrantana; Francis L. Masselle; Edwin T. Grimes

[57] ABSTRACT

An improved slide holder for use with a clinical spinner comprises a support having a channel defined in the top thereof transverse to the vertical axis of rotation of the support. Rapid rotation of the support with a slide positioned over the channel effects a partial vacuum in the channel which tends to hold the slide tightly against the support. Mechanical stops and spring retainers may also be included to insure retention of the slide on the support. The design of the slide holder minimizes the formation of an aerosol during spinning. A disposable spin-off interception system cooperates with the slide holder's operating characteristics to effectively eliminate aerosol formed.

22 Claims, 10 Drawing Figures

U.S. Patent  Aug. 1, 1978  Sheet 1 of 2  4,103,643
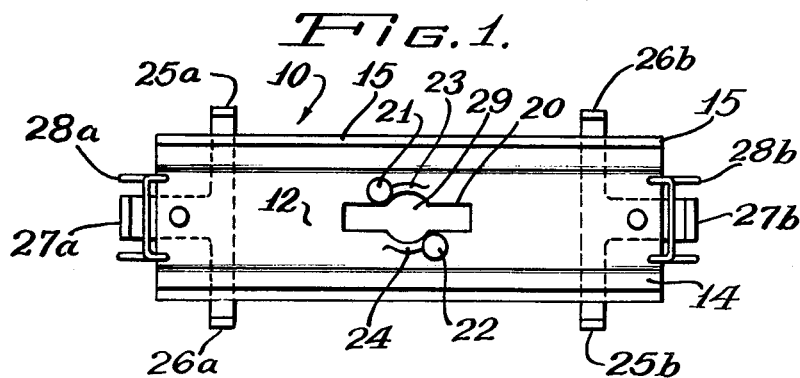
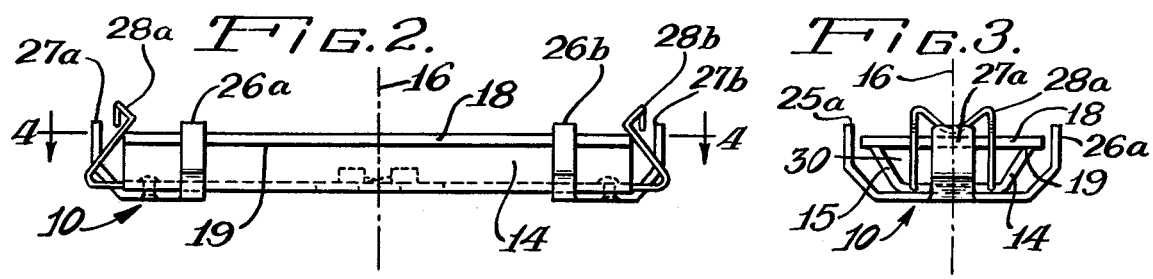
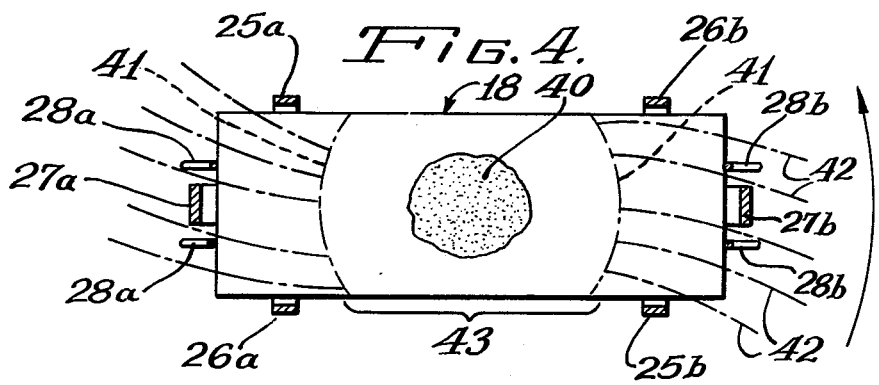
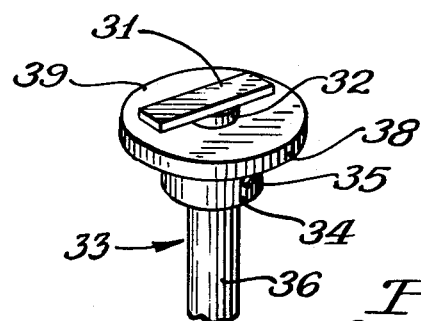
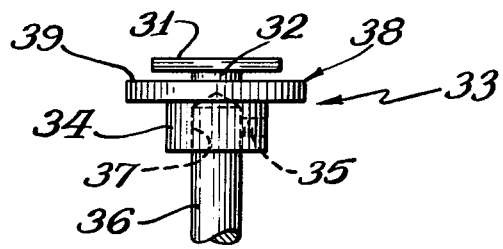
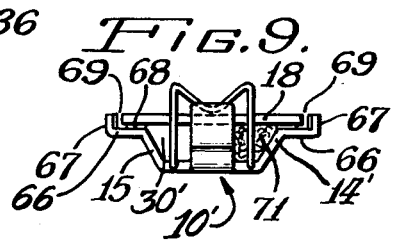
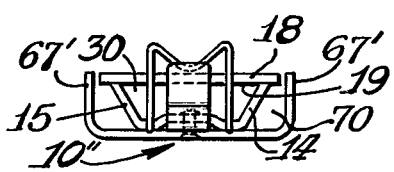

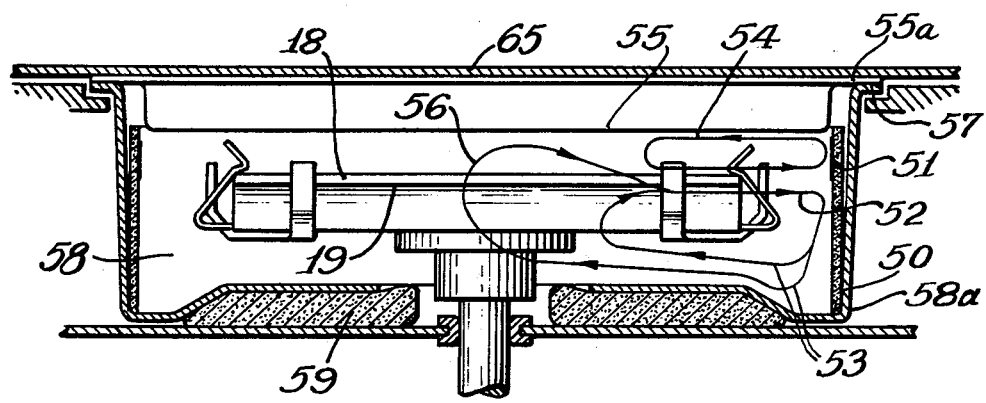
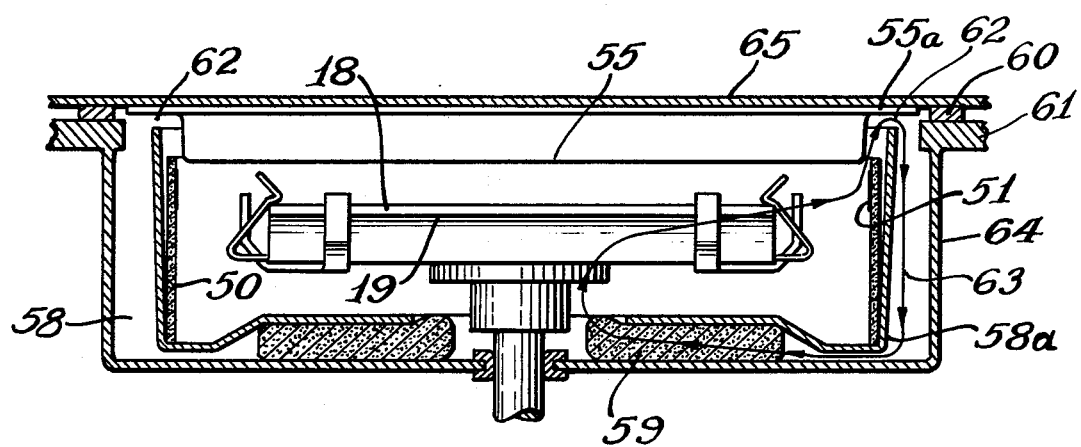

AEROSOL-REDUCING SLIDE HOLDER SYSTEM

This is a continuation of application Ser. No. 428,295, filed Dec. 26, 1973, now abandoned, which itself is a continuation of application Ser. No. 341,347, filed Mar. 15, 1973 and now abandoned.

BACKGROUND OF THE INVENTION

This invention relates to an improved apparatus for holding a planar microscope slide during rapid rotation in preparation of a thin uniform monocellular layer sample or specimen on the surface of the slide and an improved system cooperating with the slide holder for handling the spin-off therefrom.

The use of a centrifuge or spinner to prepare a thin uniform layer of a liquid such as blood or a solution of plastic or of photoresist is well known. For example, U.S. Pat. No. 3,577,267 describes a method for preparing a monocellular layer of blood by means of such a spinner.

In the practice of making thin layer blood smears for clinical examination, it is important to make the process of inserting a clean slide into the spinner as simple as possible to conserve time and labor and to minimize handling of the slide before the sample is spun. This follows since any finger print or other hydrophobic deposits on the slide will interfere with the formation of a uniform sample layer. Additionally, the slide holder must be able to transmit rapid accelerations to the slide without chipping or damaging the slide. Also, the slide must be held positively and securely to eliminate fluttering or disengagement from the slide holder at high speeds causing breakage of the slide and a possible hazard to the operator.

Another important consideration in the design and configuration of a slide holder is the fact that spin-off of a liquid from a rotating surface disposed perpendicularly to the axis of rotation is a well-known method of producing an aerosol. This aerosol may be a cloud of liquid droplets ranging from large irregular masses to air-borne drops of 10 microns or less in diameter according to conditions of speed of rotation, viscosity and surface tension of the liquid, presence of projecting impact surfaces and other factors. Aerosols in the size range under 10 microns may be air-borne for a considerable length of time. If the droplets should contain a hazardous substance, a risk may exist to personnel in the laboratory where the spinner is in use.

A slide holder, therefore, should be designed to minimize the formation of such hazardous aerosols and, if possible, to cooperate in the trapping and suppression of the aerosol, if generated, by functioning within a system which can intercept and retain the aerosol as well as more massive spin-off.

Still another requirement for a slide holder is that it should have low rotational inertia to permit rapid acceleration and to minimize coasting time of the holder after the spin and sample preparation is completed.

U.S. Pat. No. 3,577,267 cited above suggests that a vacuum may be applied to the lower surface of the slide to hold the slide in position on the spinning support holder. The patent discloses the use of a vacuum pumping mechanism and because of the specific construction disclosed, a rather powerful motor is required to provide adequate acceleration to the sample. The present invention provides a construction which is simplified in comparison to the prior art yet which provides the advantages that follow from the use of a vacuum for holding a slide sample in position.

SUMMARY OF THE INVENTION

In a principal aspect then, the present invention provides a support means for a planar slide. The support means includes a cavity with a passage extending therefrom transverse to the vertical spin axis of the support means. Rapid spinning of the support means with the planar slide positioned thereon will cause air to be discharged from the cavity through the passage, thereby creating a partial vacuum within the cavity. The planar slide is thus biased against the support means by the normal atmospheric pressure acting on the top surface of the slide. A mechanical retainer and drive means may also or alternatively be provided on the support means for positioning the planar slide and holding it in position during acceleration and deceleration of the holder.

It is thus an object of the present invention to provide an improved slide holder.

It is a further object of the present invention to provide an improved slide holder of simplified construction which utilizes a vacuum principle to retain the specimen slide in position on the holder during a spinning operation.

Still another object of the present invention is to provide an improved slide holder which may include mechanical retaining means for positioning the slide on the holder.

A further object of the present invention is to provide a slide holder which may be of a minimum size and weight in order to obviate any problems attributable to inertia such as slow acceleration and deceleration of the holder.

Still a further object of the present invention is to provide a slide holder system which minimizes the effect of any hazardous aerosols which may be generated during the spinning operation.

Yet a further object of this invention is to provide in this improved slide holder a cooperative structure which functions to assist in the clean-up of hazardous aerosols, should they be generated, in collaboration with a suitable trapping system.

These and other objects, advantages and features of the invention will be set forth in the detailed description which follows.

BRIEF DESCRIPTION OF THE DRAWING

FIG. 1 is a top plan view of the improved holder of the present invention;

FIG. 2 is a side elevational view of the improved holder of the present invention;

FIG. 3 is an end view of the improved holder of the present invention;

FIG. 4 is a cross-sectional view taken along the line 4—4 in FIG. 2 illustrating the spin pattern that results upon rotation of the holder of the present invention with a sample thereon;

FIG. 5 is a perspective view of a hub mechanism for attaching the holder of the present invention to a drive shaft or a spinner motor;

FIG. 6 is a side elevation of the mechanism for attaching illustrated in FIG. 5;

FIG. 7 is a side elevation of a spinner chamber illustrating aerosol travel paths inside the spinner chamber;

FIG. 8 is a side elevation of an alternative embodiment of the spinner chamber illustrating aerosol travel paths in an auxiliary aerosol trapping system;

FIG. 9 is an end view of an alternative embodiment of the slide holder which facilitates aerosol removal; and FIG. 10 is an end view of still another alternative construction of the slide holder portion of the total slide holder portion of the total slide holder system.

DESCRIPTION OF THE PREFERRED EMBODIMENT

Referring first to FIGS. 1–4, the slide holder of the present invention comprises a body or support means 10 in the shape of an elongated channel. The body 10 is defined by a horizontal substantially planar bottom wall 12 and vertically ascending side walls 14 and 15 respectively. In the preferred embodiment, side walls 14 and 15 extend angularly upward from bottom wall 12 and terminate in horizontal edge surfaces lying in and defining a plane which is transverse to a vertical slide spin axis 16 as shown in FIG. 2 and 3. A slide 18 having a lower planar surface 19 may thus be positioned on the top edges or surfaces of the side walls 14 and 15 as shown in FIG. 2 and 3.

Since the typical plane dimensions of a slide 18 are generally 1 inch by 3 inches, the dimensions of the support 10 at the upper edges of side walls 14 and 15 are also 1 inch by 3 inches, so that the slide 18 may be properly supported by the side walls. Moreover, during operation the holder becomes a vacuum pump as walls 14 and 15 tend to sealingly engage surface 19 to permit development of a partial vacuum as will be explained in more detail later.

The depth of the channel formed by bottom wall 12 and side walls 14 and 15 is typically about ⅛ inch, although greater or lesser depths consistent with aerosol control may be used in order to keep the mass and rotational inertial and also the windage of the device low so that driving power requirements will be modest. The supporting edges of walls 14 and 15 are spaced apart almost the width of the slide 18 so that as much of the area of the slide as practical will span between the walls without an edge of the slide dropping into the channel defined by the side and bottom walls.

Bottom wall 12 of the holder contains a key slot 20 shaped to receive a locking member 31 and a hub 32 of holder attachment means 33 in the manner explained herein below. A pair of stops 21 and 22 are positioned adjacent to, and on opposite sides of, slot 20 and at the upper end of a pair of oppositely inclined surfaces 23 and 24, respectively, which extend upwardly from the top surface of wall 12.

Body 10 may be made of metal or any light strong material such as a plastic. A plastic such as glass-filled nylon or polycarbonate is well suited since it is corrosion-resistant, easy to clean, has high impact strength and is easy to fabricate by injection molding techniques. These plastics, being strong but flexible, also conform to the plane of the bottom surface of the slide during operation.

At each end of the channel and on opposite sides thereof, respective projections 25a and 25b are provided which may engage the edge of slide 18 at the beginning of a spin. Also at each end of the channel opposite single projections 25a and 25b are respective single projections 26a and 26b positioned to engage the edge of slide 18 during deceleration at the end of a spin. Projections 25a, b and 26a, b serve the described functions when the holder is being spun in the counterclockwise direction; of course, spinning in a clockwise direction would result in no difference to operability of the device, although the functions of the projections 25a, b and 26a, b would be interchanged.

Although the projections 25a, b and 26a, b may be fashioned from separate metal clips which are attached to support 10, they may also be molded or otherwise formed integrally with the support. Because slide dimensions may vary, a clearance should be provided between projections 25a, b and 26a, b and the edges of the slide 18 so that free play of the slide between projections is possible.

At each end of support 10, a respective stop 27a, 27b and keeper spring 28a, 28b are provided. Slide 18 is inserted by positioning one end under the spring 28a or 28b at one end of support 10 and moving the slide longitudinally to push back those springs while pushing the other end of the slide down to snap under springs at the opposite end of the support. Slide 18 may thus be placed in position on, and in close surface contact with, the co-planar upper edges of walls 14 and 15 of the holder to form a cavity 30 with opposite ends open to the atmosphere.

Typically, springs 28a, b may be fabricated of 0.014 inch diameter music wire designed to require a longitudinal force of 0.5 to 1.5 pounds on the slide during insertion into or removal from the holder. This system, despite the spring stops 27a, b, is stable against normal off-balance centrifugal force due to longitudinal slide displacement. Since such displacement of the slide causes a nearly linear restoring force from springs 28a, b whereas the centrifugal force is proportional to the square of slide displacement, it may be shown that at low displacements the spring generated restoring force will prevail. Hence, the system is stable. Stops 27a, b are provided to limit end movement when disengaging the springs 28a, b so that the springs will not be accidentally overstressed.

The structure for two methods of securing the slide 18 has thus far been described. These methods are (1) self-generated partial vacuum, and (2) mechanical retention by keeper springs 28a, b. Each of these, in the form described, is effective. Each could be used alone as the slide retention means. Together they cooperate to produce improved results. As will be shown presently, in conjunction with a detailed discussion of the vacuum holding method, either method can be associated with an aerosol control system in which the slide holder plays an intrinsic part.

To clarify this, with regard to the holding function, consider the all mechanical form of the holder not provided with an open-ended cavity under the slide. Even without the partial vacuum, the slide would be retained and driven effectively. However, at high speeds the slide would tend to flutter under the action of air buffeting. This would deteriorate the uniformity of the monolayer. Also, air would tend to flow under the slide 18, if it were lying on a flat surface, and lift the slide. Then, any off-balance of the slide could cause radial oscillation in a horizontal plane since there would be little friction between slide and holder. In the transition between acceleration and uniform speed drive, the slide would slam from one set of projections (25a, b and 26a, b) to the other nicking the slide edge, possibly breaking it. By adding vacuum hold-down, however, these effects are prevented at the high speeds where they are most objectionable. Basically, then, the above description discloses a novel slide holder which uses a self-generated pressure differential to hold the slide during rotation and cooperating keeper springs to insure this holding function during low suction parts of the run cycle.

Referring now to FIGS. 5 and 6, there is illustrated an assembly 33 for attachment of the support or holder 10 shown in FIGS. 1 through 4 to the spin drive means. Attachment assembly 33 comprises a mounting hub 34 which has a coaxial blind bore 37 receiving one end of a drive shaft 36 secured therein by means as a set screen 35.

Mounting hub 34 includes a central plate 38, disc-shaped for easy manual grasping by an operator to facilitate positioning of the attachment assembly 33 on drive shaft 36 as well as mating of the holder 10 with the attachment assembly 33. Plate 38 includes a planar top surface 39 that supports and aligns the under surface of the slide holder 10 to prevent wobble which would impair preparation of uniform spin smears. Surface 39 also forms an air seal to the under surface of the holder to prevent air leakage through mounting slot 20 into the slide holder cavity which would cause loss of slide-holding vacuum.

Extending upwardly from surface 39 of plate 38 is a cylindrical projection or hub 32 which is adapted to engage the center portion 29 of holder mounting slot 20. Projection 32 has an axial dimension equal to the thickness of wall 12, typically 1/32 of an inch, and provides axial centering of holder 10.

Atop hub 32 is a bar-shaped locking bar member 31 which is adapted to fit through holder slot 20 for rotation along inclined surfaces 23 and 24 to lock holder 10 tightly in position on attachment assembly 33. Member 31 is thus turned crossways in the manner of a bayonet catch to secure slide holder 10 to attachment assembly 31. When slide holder 10 is rotated relative to projection 32, wedging action locks the holder firmly to projection 32 and forces the sealing, aligning surface 39 tightly against the bottom surface of the holder.

Stops 21 and 22 prevent rotation of holder 10 in the wrong direction and also prevent an operator from rotating the assembly 33 too far in one direction during installation. The rotational direction of the driving means locks holder 10 and surfaces 23 and 24 prevent unlocking when decelerating. Removal and replacement of the holder by hand, however, is effected without tools in a matter of seconds by a quarter turn of the holder 10. Cleaning is greatly facilitated by the ready removal of the holder 10 from assembly 33.

This arrangement provides for axial centering of the slide holder and eliminates unbalanced vibration which would jeopardize the security of the slide and also hinder development of good spin smears.

In operation, when slide holder 10 starts to rotate in response to driving of shaft 36, the slide will tend by its own inertia to stay in contact with the edges of walls 14 and 15, but will slide horizontally relative to the cavity defined by the walls 12, 14 and 15 until driven by the accelerating hooks or projections 25a, b. As speed builds up, typically to a selected full speed of 2000-6000 rpm in about 80 milliseconds, the air in the cavity or channel formed by the slide 18 and the walls 12, 14 and 15 will be expelled from the ends of this cavity by centrifugal force. This forms a partial vacuum within the cavity. The difference between the internal and external pressure of this cavity tends to press the slide 18 securely against the top edges of the walls 14 and 15 with a force that varies from about 40 grams at 2000 rpm to 360 grams at 6000 rpm. This force will not only hold the slide 18 firmly in place against walls 14 and 15 but will also cause the walls, made from a compliant material such as nylon or polycarbonate, to conform to slide 18, thus sealing the edges even more effectively. Nonetheless, even if channel walls 14 and 15 are of a rigid material such as metal, the high volumetric capacity centrifugal pump formed by the configuration of the holder will still maintain lowered pressure within the cavity despite moderate leakage. Should higher operating speeds be desirable for specialized purposes a controlled leak can be incorporated near the center of the holder, as by use of a capillary sized hole, to prevent the suction from rising to a value at high speed that could break the slide.

During declaration of the holder, the partial vacuum is maintained but less effectively as speed decreases. If deceleration is rapid, the slide will normally shift over to engagement with the decelerating hooks or projections 26a, b.

Although the above description of the structure of the present invention calls for the inclusion of keeper springs 28a, b and stops 27a, b, it is possible to utilize the invention without this structure. Tests have shown that such keeper springs are not required although, it not used, occasionally a slide can escape from the holder when not properly positioned or seated on holder 10 at the start of the spin. Thus, the preferred embodiment includes keeper springs 28a, b since they serve to center the slide as well as hold it down during the initial acceleration and final deceleration stages.

As an example of a further advantage, holder 10 also meets the requirement of a minimum amount of interception of blood or other specimen being spun off, this interception being by reason of projections above the plan of the slide top surface. FIG. 4 shows a typical spin-off pattern in diagrammatic form. In making a typical blood smear spin run about two drops, 120 microliters, of blood is placed in the center of a clean hydrophyllic slide 18 on the holder 10. Gravity spreads this into an initial pool 40.

When the run starts, a rate of acceleration high enough to reach 4000 to 5000 rpm in 80 milliseconds is applied to the slide 18. Centrifugal force first expands the pool approximately as shown by the dotted outline 41. Surface tension opposes this expansion and is finally overcome at one or more regions of the outline margin.

If the slide is clean, the ends of the pool may almost reach the ends of the slide by the time about 80% of the liquid leaving the monolayer, a few microns thick, breaks away at the lateral edges of the slide and is spun off. The residual excess continues to expand toward the edges and ends of the slide as rotation continues at a steady speed. If the slide is not clean, this excess will straggle off along curved paths such as 42; otherwise it may cover the whole slide.

The initial spin-off will be in relatively large drops and irregular jets which will fly off and form a wet horizontal streak, 51 as shown in FIG. 7 and 8, circumferentially along the length of a blotter liner strip 50. If any of these large masses of liquid are intercepted in flight by projections about the plane of the slide, they may be dispersed into smaller droplets contributing to possible aerosol. The major part of this spin-off takes place along the sides of the slide in region 43 (FIG. 4) where the surface tension builds up earliest. The slide holder of the present invention is free from intercepting projections in this region.

If utmost freedom from interception is mandatory, a version of the slide holder can be provided on which the drive hooks and stops 25a, b, 26a, b and 27a, b are restricted in height to just below the plane of the upper surface of the slide 10 thereby reducing interception to the negligible amount intercepted by the vertical members of keeper springs 28a, b. In practice, this limits the permissible dimensional latitude of the slides used and requires greater precision of manufacture. Greater care in loading is also necessary to insure the slide does not rest on top of projections 25a, b and 26a, b.

Thus, while the invention can be by design substantially free from all aerosol generating projections, a compromise height of about 3/32 inch or twice the slide thickness above the side wall edges 14 and 15 is more satisfactory in actual clinical practice. Since some small amount of spin-off interception will then occur, the preferred embodiment spaces the vertical driving projections or hooks 25a, b and 26a, b away from the edges of walls 14 and 15 to avoid suction of sample under the slide edges into the vacuum cavity and to provide a free path for centrifugally driven air to sweep these members clean.

Another possible source of aerosol is the spin-off of the residual during the steady speed part of the run. This residual reaches the edge of the slide as a thin sheet of liquid which, after leaving the edge, breaks up into droplets. Aerosol generated in this manner and in the range below 10 microns diamter must be retained in the spinner chamber and must be trapped or absorbed before the cover of the chamber is opened after a run. This aerosol cannot be removed in the obvious manner by ventilating the chamber since to do so would endanger the morphology of the red cells by premature drying of the monolayer, as indicated in U.S. Pat. No. 3,705,048.

Unexpectedly, the structure of slide holder 10 cooperates effectively with a disposable spin-off interception system in removal of the undesired aerosol as well as to minimize its generation. Referring to FIG. 7, the method by which this is done is the recirculation of the aerosol within a spinner chamber 58 defined by a plastic cup 58a so as to repeatedly bring the aerosol into contact with the wet surface of an absorbent blotter strip 50. The outside shape of slide holder 10 makes it an effective centrifugal pump for adjacent air causing a radial air flow within chamber 58 as indicated by arrow 52 which carries the aerosol laden air out and throws it against the wet area 51 of the blotter liner 50 where the aerosol adheres on contact. Return air flow, represented by arrow 53, is mostly below the slide holder 10, the circulation indicated by arrow 54 above the holder being restricted by a cover shield 55 on cover plate 65 as taught in previously referenced U.S. Pat. No. 3,705,048.

Because of the rectangular shape of slide holder 10 enough return air, represented by arrow 56, is also available in the central region on either side of the holder to scavenge the aerosol, low in this region, without excessively drying the monolayer. Experimental observation of the spatters found on the outer part of cover shield 55 and the outer part of the bottom of cup 58a indicates the air flow paths and shows that the whole flow mass rotates with the slide holder as a unit. This permits complete aerosol cleanup while not drying the monolayer excessively. Also, humidity picked up by the air from the preferably wet liner strip 50 retards drying effects.

Surprisingly, the clearance or removal of any aerosol formed is effected by the circulation set up by the slide holder in the brief time, e.g., 2 seconds, during which the motor is running. Laboratory tests using bacterially and virally infected samples have established that, with this slide holder and scavenging system, residual aerosol is too low to be detected when cover 65 is opened after a run. However, this same pumping action of the slide holder which causes the aerosol cleanup circulation could force aerosol out into the laboratory. To prevent this, sealing surface 55a is provided on cover shield 55 which mates with a sealing rim 57 on cup 58a which rests on a cup support 59, an annulus of resilient open cell plastic foam. The upward push of support 59 provides the sealing force when compressed by cover closure 65.

Should added aerosol trapping be required or should removal of a hazardous solvent be necessary, an extension of the recirculation system, still using the slide holder as a pump, is possible as shown in FIG. 8. The cover seal is here moved outward and comprises, for instance, a closed cell foam ring 60 disposed between cover plate 65 and the top of an instrument table 61. An annular opening 62 allows the pumped air, arrow 63, to be circulated downwardly between the vertical slide wall of cup-58a and an outer cup 64 and returned through cup support 59. Support 59 may be treated, if necessary, to act as an absorption filter removing undesirable components carried by the air system illustrated by arrow 63. This outer scavenging system augments the internal system previously described both being made effective by the design of slide holder 10 as a pump.

A still further method of aerosol control results from the vacuum generating ability of slide holder 10. As illustrated by the embodiment of FIG. 9, the side walls 14', 15' of holder 10' include lateral extensions 66 connected with upwardly turned vertical flanges 67 extending along the length of the slide 18. Flanges 67 do not project above the slide. Extensions 66 and flanges 67 are spaced from the bottom and edges of the slide by ribs or projections 68 or, alternatively, by curving the flanges away from the center of the slide. This provides suction intake aperatures 69 typically of the order of 0.5 mm wide through which aerosol from the slide will be drawn by the pumping action of the rotating slide holder.

This aerosol will then be discharged at the ends of holder 10 to be trapped on the wet area 51 of the blotter strip 50 or it may be intercepted by treated porous disposable filter units 71 placed in the holder channel beneath the slide near the ends to absorb the aerosol. In the form of FIG. 9, retention of the slide 18 may be mostly mechanical since the suction cavity 30', being primarily effective in aerosol removal, will be lowered by the controlled leakage aperatures 69 at the lateral edges of the slide 18.

To avoid reduction of vacuum retention of the slide that may be caused by the structure shown in FIG. 9, a modification, shown in FIG. 10 provides for separation of the hold-down vacuum-generating cavity 30 from a vacuum channel 70 for aerosol scavenging. Walls 14 and 15 of holder 10" seal against slide surface 19 as heretofore set forth. The scavenging channel 70 defined by flanges 67' may surround the retention cavity as shown. Alternatively, two separate channels (not shown) may be positioned laterally one being disposed on each side of retention cavity 30.

In both forms, FIG. 9 and 10, flanges 67 and 67', respectively may perform the function of projections 25a, b and 26a, b shown in the embodiment of FIG. 1.

While in the foregoing there has been set forth a preferred embodiment, it is to be understood that the invention shall be limited only by the following claims and their equivalents.

What is claimed is:

1. Apparatus for holding a planar specimen slide during rotation by drive means comprising, in combination:

support means for said slide; and means for attaching said support means to the drive means so that said support means may be rotated about a substantially vertical axis by said drive means, said support means including a cavity with at least one passage transverse to the vertical axis, mechanical means for at least lightly retaining said slide to said support means, said support means also including U-shaped ascending walls defining said cavity, said walls terminating in a substantially planar surface transverse to said axis for abutment with said planer slide so that positioning of said slide on said support means forms a tubular configuration having the ends thereof open to the atmosphere and rotation thereof by said drive means causes air within said configuration to be discharged via said open ends thereby creating a partial vacuum that tends to adhere said slide to said support means.

2. The apparatus according to claim 1 wherein said means for attaching said support means to said drive means comprises a rotatable interlocking member adapted to engage said support means.

3. The apparatus according to claim 2 wherein said interlocking member includes stop means for limiting the sense and degree of rotation thereof.

4. The apparatus of claim 1 wherein said mechanical means comprises spring means for engaging and mechanically retaining said slide on said support means.

5. The apparatus of claim 4 including means for limiting the flexure of said spring means during positioning of said slide on said support means.

6. The apparatus of claim 1 wherein said slide holder is rectangularly shaped.

7. Apparatus for holding a planar specimen slide during rotation by rotary drive means comprising, in combination:

slide support means attachable to said drive means for rotation in a substantially horizontal plane about a substantially vertical rotation axis;

a pair of spaced, substantially parallel, upwardly extending walls projecting from said support means for engagement with said slide to form therewith a tubular configuration having ends thereof open to the atmosphere;

biasing means for also engaging said slide on said support means and maintaining said slide in substantially fixed position to restrict vertical and horizontal displacement of said slide from said support means, said biasing means including means for manual displacement thereof to insert and retract said slide from said support means; and means to rotate said support at a speed to induce a partial vacuum within said tubular configuration to thereby fix the slide on said support during rotation thereof.

8. The apparatus of claim 7 wherein said biasing means comprises a pair of spring members for engaging opposite ends of said slide and biasing said slide toward said support means as well as toward one another.

9. The apparatus of claim 7 including mechanical stop means attached to said support means for limiting the strain on said biasing means.

10. A slide holder system for collecting aerosol generated during rotation by drive means of a planar specimen slide, comprising, in combination:

a slide holder comprising an elongated, horizontal bottom wall having a pair of spaced vertical walls extending upwardly therefrom;

said planar slide being supported on said pair of walls to thereby form, with said holder, a horizontally disposed tubular structure having open ends for producing during rotation a partial vacuum that adheres said planar slide onto said pair of walls;

mechanical means to at least lightly retain said slide on said vertical walls;

means for enclosing said slide holder including circumferential chamber means and a cover, said cover being spaced above the rotational path of said holder; and absorption means positioned about said slide holder in the plane of rotation of said slide to absorb aerosol projected from said slide during rotation thereof.

11. The system of claim 10 including a second chamber surrounding said first chamber with said cover being sealed only with said second chamber.

12. The system of claim 10 including a second outer chamber surrounding said first chamber and defining a fluid flow circulation path between the walls of said chambers, at least of said path including intersecting filter material for collecting aerosol from the fluid circulating therein.

13. The system of claim 12 wherein said second outer chamber communicates with said horizontally disposed tubular structure near the center of said horizontally disposed tubular structure.

14. The apparatus of claim 10 including means communicating with said horizontally disposed tubular structure to remove, by suction, aerosol generated at the lateral edges of said slide during rotation thereof.

15. A slide holder system for collecting spin-off material, including aerosol generated during rotation by drive means of a planar specimen slide comprising, in combination:

a slide holder including means attached to said drive means for supporting said slide, and means for biasing said slide against said holder during rotation of said slide holder, said means for biasing including mechanical means to at least lightly retain said slide onto said slide holder and means for providing a relatively lower pressure condition on substantially the entire lower surface of said slide than on substantially the entire upper surface of said slide and mechanical hold-down means to mechanically hold said slide on said holder;

means for enclosing said slide holder including cup means defining a circumferential chamber and a cover for said chamber, said cover being spaced above the rotational path of said holder; and circumferential absorption means positioned about said slide holder in the plane of the rotational path thereof to absorb material projected by said slide holder and flowing in said chamber in response to internal fluid path current generated by rotation of said slide holder.

16. The system of claim 15 wherein said cover is sealed to said cup means.

17. The system of claim 15 including means defining an outer chamber surrounding the first chamber and means sealing said cover with said outer chamber only.

18. The system of claim 16 including passage means communicating with the region of said lower pressure to remove, by suction, aerosol generated at the lateral edges of said slide.

19. A slide holder system for collecting spin-off material, including aerosol generated during rotation by a drive means of a planar specimen slide comprising, in combination:
- a slide holder including means attached to said drive means for supporting said slide, and means for biasing said slide against said slide holder during rotation of said holder, said means for biasing including mechanical means to at least lightly retain said slide onto said slide holder and means for providing a relatively lower pressure condition on substantially the entire lower surface of said slide;
- means for enclosing said slide holder including cup means, defining a circumferential chamber, and a cover for said chamber, said cover being spaced above the rotational path of said holder;
- means defining an outer chamber surrounding said first chamber and defining therewith a fluid flow circulation path between the walls of said chambers, and a body of filter material intersecting at least a portion of said path.

20. The system of claim 19 wherein said body of filter material is disposed in said second chamber and constitutes a support on which the cup means is mounted.

21. A slide holder system for collecting spin-off material, including aerosol generated during rotation by a drive means of a planar specimen slide comprising, in combination;
- a slide holder including means attached to said drive means for supporting said slide, and means for biasing said slide against said holder during rotation of said holder, said means for biasing including mechanical means to at least lightly retain said slide onto said slide holder and means for providing a relatively lower pressure condition on substantially the entire lower surface of said slide than on substantially the entire upper surface of said slide;
- means for enclosing said slide holder including cup means defining a circumferential chamber, and a cover for said chamber, said cover being spaced above the rotational path of said holder;
- circumferantial absorption means positioned about said slide holder in the plane of the rotational path thereof to absorb material projected by said slide holder and flowing in said chamber in response to internal fluid path current generated by rotation of said slide holder; and
- means placing in communication at least a portion of the edges of said slide with said means for providing a relatively lower pressure to thereby draw aerosol generated at the edges of said slide and to discharge said aerosol to said circumferential absorption means.

22. The system of claim 21 including aerosol absorption means disposed in said slide holder.

* * * * *